United States Patent [19]

Ams

[11] Patent Number: 4,919,621

[45] Date of Patent: Apr. 24, 1990

[54] PLUG AND SOCKET TYPE CONNECTOR FOR CONNECTING AN ENDOSCOPE TO SUPPLY UNITS

[75] Inventor: Felix Ams, Kämpfelbach, Fed. Rep. of Germany

[73] Assignee: Richard Wolf, GmbH, Fed. Rep. of Germany

[21] Appl. No.: 271,924

[22] Filed: Nov. 16, 1988

[30] Foreign Application Priority Data

Nov. 16, 1987 [DE] Fed. Rep. of Germany ....... 3738633

[51] Int. Cl.[5] .............................................. A61B 1/06
[52] U.S. Cl. ...................................... 439/191; 128/6; 350/96.20; 439/595; 439/924
[58] Field of Search ............... 439/190, 191, 166–173, 439/577, 595, 924; 350/96.20, 96.21, 96.22, 96.26; 128/6

[56] References Cited

U.S. PATENT DOCUMENTS

| | | | |
|---|---|---|---|
| 4,327,964 | 5/1982 | Haesly et al. | 350/96.20 |
| 4,416,268 | 11/1983 | Hagino | 128/6 |
| 4,422,702 | 12/1983 | Nordeen | 439/191 |
| 4,432,604 | 2/1984 | Schwab | 350/96.20 |
| 4,469,393 | 9/1984 | Chewning, Jr. | 439/717 |
| 4,597,627 | 7/1986 | Wondra et al. | 439/174 |
| 4,616,631 | 10/1986 | Takahashi | 128/6 |
| 4,617,915 | 10/1986 | Arakawa | 128/4 |
| 4,618,195 | 10/1986 | Keane | 439/191 |
| 4,804,243 | 2/1989 | Borsuk et al. | 350/96.20 |

FOREIGN PATENT DOCUMENTS 0037013 3/1981 European Pat. Off. .
3624442 2/1987 Fed. Rep. of Germany .

*Primary Examiner*—Neil Abrams
*Attorney, Agent, or Firm*—Hill, Van Santen, Steadman & Simpson

[57] ABSTRACT

A plug and socket type connector for connecting an endoscope to supply units such as light projectors, pumps and electrical generators, comprises a casing incorporating connections which may be coupled to corresponding connections of the supply unit or units in question, and the casing is provided with a reception device for releasably connecting a plug of a light conductor cable to the casing.

8 Claims, 1 Drawing Sheet

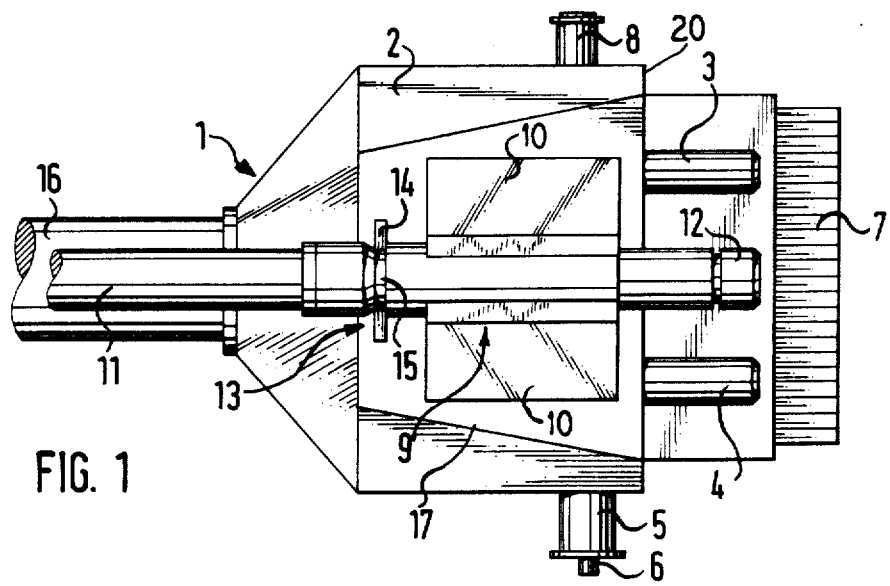
FIG. 1
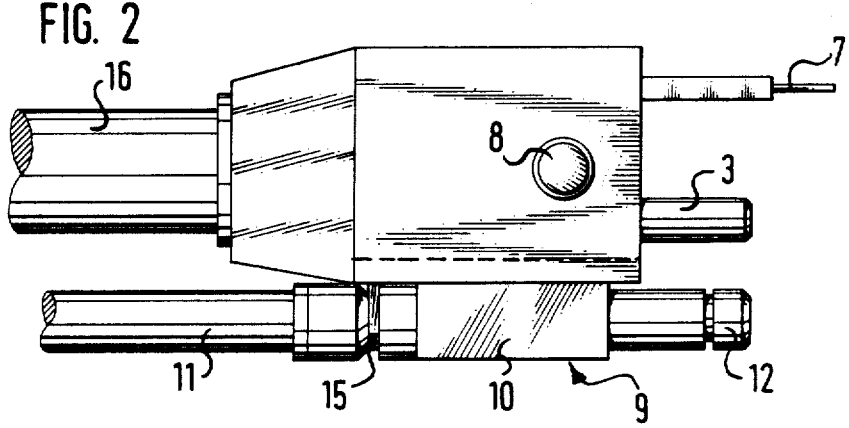
FIG. 2
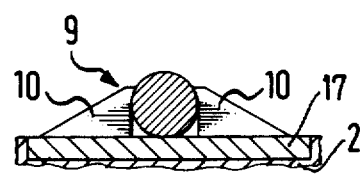
FIG. 3
FIG. 4

PLUG AND SOCKET TYPE CONNECTOR FOR CONNECTING AN ENDOSCOPE TO SUPPLY UNITS

BACKGROUND OF THE INVENTION (a) Field of the Invention

This invention relates to a plug and socket type connector for connecting an endoscope to supply units such as light projectors, pumps and electric generators, comprising a casing provided with connections which may be coupled to the corresponding supply unit or units connections.

(b) Description of the Prior Art

For the purpose of connecting a flexible endoscope to the supply units such as a light source, a suction and scavenging pumps, these are provided according to the prior art with a supply duct secured in the control casing of the endoscope, of which the distal extremity is divided into two separate supply ducts incorporating appropriate plug and socket type connectors. This division is needed because the required light source and the suction and scavening pump commonly consist of two separate supply units which lack any common coupling section, even if, for example, these are jointly installed in an instrument trolley or the like, or placed in the same in the form of plug-in instrument units.

On the other hand, since composite units comprising a light source and a suction and scavenging pump installed in a common casing with a combined coupling section and connector sockets or the like installed thereon, are also in use, flexible endoscopes cannot generally be utilized with supply units of this nature.

SUMMARY OF THE INVENTION

For the purpose of avoiding the disadvantages of the prior art, the main object of the present invention consists in devising the structure of a plug and socket type connector in such a manner as to provide a means of connecting a flexible endoscope to a combined supply unit as well as to separate supply units which individually comprise a suction and scavenging pump or a light source, in which respect a possibly supplementally required control unit may optionally be situated in the light source or in the suction and scavenging pump.

To this end, the present invention consists in a plug and socket type connector for connecting an endoscope to supply units, such as light projectors, pumps and electrical generators, comprising a casing incorporating connections which may be coupled to corresponding connections of the supply unit or units in question, characterized in that a reception element for releasable connection of the plug of a light conductor or ductor cable to the cable is provided on the casing of the plug and socket type connector.

By means of the invention, there are obtained the advantages which consist in particular in the adaptability of the plug and socket type connector to the momentarily encountered form of the supply units, a neat layout, stowage and combination of the supply ducts being obtained with uncomplicated, reliable and rapid handling means.

These advantages come into effect especially if the receiving element or section of the reception element comprises elastically deformable gripping jaws, which form an insertion slot for the plug of the light conductor or ductor cable and clamp the latter and if the plug is secured against axial displacement by means of a retaining means engaging the plug in a shape-locked manner.

Provision may be made in a preferred modified embodiment for the receiving section combined with the retaining means for axial immobilization to be releasably connected to the casing, thereby establishing the possibility that the receiving section for the plug of the light ductor cable may in the case of a separate connection of the same, be removed from the casing to prevent a possible obstruction during handling.

Provision may finally be made for the purpose of improving the connection reliability and of providing a compact form. Thus, the connections for electrical supply are combined in a plug bar or the like, and are situated in the end-side extremity of the plug and socket type connector like the other connections.

BRIEF DESCRIPTION OF THE DRAWINGS

In order that the invention may be more readily understood, an embodiment thereof will now be described, by way of example, with reference to the accompanying drawings, in which:

FIG. 1 is a plan view of a plug and socket type connector constructed according to the invention, with a light ductor cable coupled thereto, FIG. 2 is a side elevational view of the plug and socket type connector of FIG. 1, FIG. 3 is a cross-sectional view showing the receiving section for securing the light ductor cable to the plug and socket type connector, and FIG. 4 is a cross-sectional view showing the retaining means for securing the light ductor cable in an axial direction.

DESCRIPTION OF THE PREFERRED EMBODIMENT

Referring to FIG. 1 of the drawings, there is shown a casing 2 of the plug and socket type connector 1, which casing 2 is provided at its end-side extremity or end 20 with a first tubular connector plug 3 for infeed of a body cavity gas. A second tubular connector plug 4 is provided for the infeed of compressed air which is ducted via an internal channel 6 of a connector 5 into a liquid reception vessel which is to be connected thereto, so that the overpressure generated thereby in this vessel may introduce the liquid into the body cavity through an annular passage formed co-axially around the channel 6.

For the purpose of transmitting electrical signals or controlling instructions and the like, a plug-type bar 7 comprising a plurality of plug-in contacts is installed at a distance from the two connector plugs 3 and 4. Another bottle-shaped receiving vessel for reception of secretions drawn off by suction from the body cavity may be connected via a laterally arranged connector 8. The casing 2 is also provided with a reception device 9 on a lateral surface. It comprises two gripping jaws 10 produced from an appropriate elastic or resilient material, which face each other whilst leaving an insertion slot extending parallel to the axis of the casing 2 leaning towards one another in the area of their top edges.

To secure a plug 12 of a light ductor or conductor cable 11 in a releasable manner, the same need merely be laid in the direction of the insertion slot on the two mutually parallel gripping jaws 10 and a light pressure applied to the same. Thanks to the pressure thereby exercised on the top edges of the two gripping jaws 10, these are spread apart resiliently, so that the plug 12 of the cable 11 is placed between the gripping jaws 10 and is releasably secured by their clamping force. So that an axial displacement of the plug 12 may now be prevented under joint insertion of the plug-in device 1 and of the plug 12 of the cable 11 into the corresponding sockets of the supply unit, a retaining means 13 comprising projections 14 is provided, which projections engage in an annular recess 15 at the proximal extremity of the plug 12 and supplementally secure the latter in an axial direction. A satisfactory, reliable and rapid connection is established between the connector 1 and the plug 12 of the light ductor cable 11, thanks to the two gripping jaws 10 on the one hand and the two projections 14 on the other hand.

As shown in FIG. 1, the reception device 9 may be combined together with the retaining means 13 in a structural component 17 which may be releasably installed on the case 2. A joint of this nature may for example be provided by means of dovetail guideways as seen in FIGS. 1, 2 and 4, which allow inserting the structural component 17 into the case 2 from its extremity 20 bearing the connectors 3 and 4.

In connection, with the invention, it should also be noted that the light conductor or ductor cable is connected to the plug 12 and that the supply duct 16 accommodates all the hose connections and electrical conductors which extend between the plug-in device 1 and the endoscope.

It should be appreciated that the invention is not limited to the embodiment herein described but includes all modifications and variations falling within its scope.

What is claimed is:

1. A plug and socket type connector for connecting an endoscope to supply units including light projectors, pumps and electrical generators, said connector comprising a casing incorporating at least one connection for coupling to at least one corresponding connection of at least one supply unit, and a reception device having means for releasably clamping a plug connection of a light conductor cable on one side of the casing, said reception device being releasably connected to said one side of the casing.

2. A plug and socket type connector according to claim 1, wherein said reception device includes retaining means for limiting movement of the plug connection along the axis thereof.

3. A plug and socket type connector according to claim 2, wherein said casing has an end with said at least one connection, said connector including a plug-type bar being provided in said end for forming connection to an electrical supply.

4. A plug and socket connector according to claim 1, wherein said case has an end with said at least one connector extending therefrom, said connector including a plug-type bar being provided at said one end to form a connector for an electrical supply.

5. A plug and socket type connector according to claim 1, wherein the means for clamping comprises elastically deformable gripping jaws, which form an insertion slot for the plug of the light conductor cable and clamp the same with said plug being secured against axial displacement by retaining means engaging the plug in a shape-locked manner.

6. A plug and socket connector according to claim 5, wherein said case has an end with said at least one connector extending therefrom, said connector including a plug-type bar being provided at said one end to form a connector for an electrical supply.

7. A plug and socket connector for connecting an endoscope to a light projector and at least one other supply unit said connector comprising a casing having a connector plug extending from one end to form a connection with said supply unit, and reception device including clamping means for releasably gripping a plug connector of a light conducting cable and including a pair of deformable jaws forming an insertion slot for receiving the plug connection, said device including retaining means having jaws engaging a groove in the plug connector to prevent axial movement of the plug connector in said slot, said reception device being releasably connected to a side of said casing.

8. A plug and socket connector according to claim 7, which includes a plug-type bar being provided on said one end of the casing to form connectors to electrical supply.

* * * * *